United States Patent [19]

Buchanan et al.

[11] Patent Number: 5,475,149
[45] Date of Patent: * Dec. 12, 1995

[54] METHOD FOR ETHER FORMATION

[75] Inventors: Robert Buchanan; Jeffrey Stults; Henry C. Lin, all of Grand Island, N.Y.

[73] Assignee: Occidental Chemical Corporation, Niagara Falls, N.Y.

[*] Notice: The portion of the term of this patent subsequent to Feb. 9, 2010, has been disclaimed.

[21] Appl. No.: 629,892

[22] Filed: Dec. 19, 1990

[51] Int. Cl.$^6$ .......................... C07C 43/00; C07C 205/00
[52] U.S. Cl. .................. 568/586; 568/585; 568/931
[58] Field of Search ................................. 568/931, 585, 568/586

[56] References Cited

U.S. PATENT DOCUMENTS

| | | | |
|---|---|---|---|
| 4,558,164 | 12/1985 | Jones et al. | 568/585 |
| 4,700,011 | 10/1987 | Pillsbury | 568/585 |

FOREIGN PATENT DOCUMENTS

| | | | |
|---|---|---|---|
| 24125 | 2/1980 | Japan | 568/585 |

OTHER PUBLICATIONS

Maki and Inukai; Gov. Ind. Res. Inst. Nagoya, Nagoya, Japan Nippon Kagaku Kaishi (3) 675–7 (Japan) 1972.
Filler et al., *J. Org. Chemistry*, vol. 26, pp. 2707–2710 (1961).

*Primary Examiner*—Marianne M. Cintins
*Attorney, Agent, or Firm*—Wayne A. Jones; Richard D. Fuerle

[57] ABSTRACT

A process for the preparation of 4,4'-dinitro-2,2'-di(trifluoromethyl)diphenyl ether according to the equation

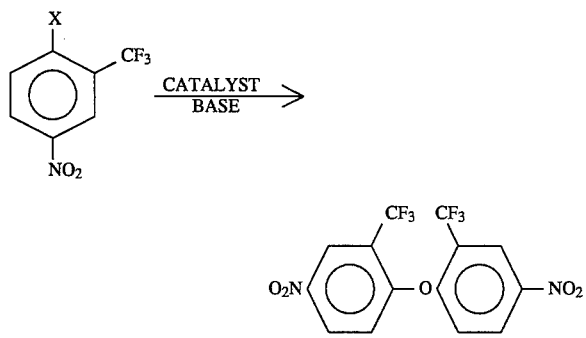

where X is F, Cl, Br or I, where the inorganic base is selected from the group consisting of alkali metal hydroxides, alkali metal carbonates, and alkali metal bicarbonates, in the presence of a catalytic quantity of a benzoate catalyst. 2,8-Dinitro-6,6,12,12,-tetrafluoro-6H,12H-dibenzo[b,f][1,5]dioxocin, the corresponding diamine and polyimides formed from the diamine are also disclosed.

28 Claims, No Drawings

METHOD FOR ETHER FORMATION

BACKGROUND OF THE INVENTION

This invention relates to a method of forming 4,4'-dinitro-2,2'-bis(trifluoromethyl)diphenyl ether (II) from 4-nitro-2-(trifluoromethyl)halobenzenes (I).

Aryl ethers have been formed by reacting aryl halides with phenols under various conditions. Roberts and Turner disclose (J. Chem. Soc., 1925, Vol. 127, p. 2004) that 2,4-dichloronitrobenzene reacts with phenol in aqueous KOH, at 100° C., to give a quantitative yield of 4-chloro-2-phenoxynitrobenzene.

R. Q. Brewster (Org. Synth. Coll. Vol. 1943, p. 445) teaches the use of copper catalyst to facilitate the reaction of excess phenol, potassium hydroxide and para-nitrochlorobenzene to form para-nitrophenyl ether.

J. D. Reinheimer, et al, disclose (J. Org. Chem., 1957, vol. 22, p. 1743) that 2,4-dinitrofluorobenzene reacts with 8-hydroxyquinoline in acetone, in the presence of triethylamine, to form 8-(2,4-dinitrophenoxy)quinoline.

D. J. Brunelle and D. A. Singleton disclose (Tetrahedron Lett., 1984, 25, p. 3383) that the reaction between sodium phenoxide and either para-fluoronitrobenzene or para-chloronitrobenzene, to form para-dinitrophenyl ether may be conducted in chlorobenzene using a phase transfer catalyst. In this case, the phase transfer catalysts studied were N-alkyl salts of 4-dialkylamino-pyridines.

Singh and Arora disclose (Tetrahedron, 1988, 44, p 2625) that para-chloronitrobenzene dissolved in toluene, may be reacted with solid potassium hydroxide to form para-dinitrodiphenyl ether. The authors observed the reaction only in the presence of catalytic quantities of various glycols. The authors indicate that the glycols act as phase transfer catalysts. The yields of the ether were poor, that is, never higher than 25%, and there was significant formation of para-chloroaniline. The authors performed mechanistic studies which led them to the conclusion that the reaction proceeded by a free radical chain mechanism.

U.S. Pat. No. 4,558,164 discloses a process for preparing a symmetrical dinitrodiphenyl ether from either ortho or para-nitrochlorobenzenes or ortho or para-nitrofluorobenzene, comprising using a polar organic solvent, a potassium salt of a fatty carboxylic acid containing 2 to 20 carbon atoms or a potassium salt of an aromatic carboxylic acid containing 7 to 12 carbon atoms as catalyst, and either sodium or potassium carbonate to react with the para-nitrochlorobenzene. The reaction is carried out at from 150° C. to 210° C. until the ortho or para-nitrochlorobenzene or ortho or para-nitrofluorobenzene reacts. Only aprotic polar solvents are useful and dimethylacetamide is the preferred solvent.

Japanese Patent 61200947 (as abstract in CA 106:156046 and in Derwent Accession number 86-275567/42) discloses a process for the preparation of 3,4'- and 4,4'-dinitrodiphenyl ether. In this process 4-chloronitrobenzene is mixed with a nitrophenol, a hydrogen chloride absorbent such as an alkaline metal hydroxide or bicarbonate, in the presence of 5 to 50 weight percent of the total material of polyethylene glycol of molecular weight 400 to 1000 or its lower alkyl ethers. The entire mixture is heated to a temperature being between 100° C. and 240° C. There is no additional solvent material used.

SUMMARY OF THE INVENTION

It has now been found that substituted benzoic acids, and substituted benzoates, when present in catalytic quantities, catalyze the reaction of 4-nitro-2-(trifluoromethyl)halobenzenes with an inorganic base and water to form 4,4'-dinitro-2,2'-bis(trifluoromethyl)diphenyl ether.

The reaction may be run in the absence of a solvent, in a dipolar aprotic solvent, or in a non-polar solvent.

DESCRIPTION OF THE INVENTION

We have now found that benzoate catalysts, that is, benzoic acids, and benzoates with electron withdrawing substituents, when present in catalytic quantities, catalyze the reaction of 4-nitro-2-(trifluoromethyl)halobenzenes and an inorganic base such as sodium carbonate, to form 4,4'-dinitro-2,2'-bis(trifluoromethyl)diphenyl ether. In addition, 2,8-dinitro-6,6,12,12,-tetrafluoro-6H,12H-dibenzo[b,f][1,5]dioxocin (bis ether) may be produced. These ethers are useful as a chemical intermediates. They can be reduced to form 4,4'-diamino-2,2'-bis(trifluoromethyl)diphenyl ether and 2,8-diamino-6,6,12,12,-tetrafluoro-6H,12H-dibenzo[b,f][1,5]dioxocin

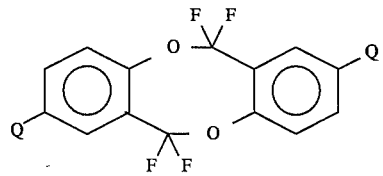

(bis ether diamine where Q is $NH_2$)

(bis ether where Q is $NO_2$)

where Q is $NO_2$ or $NH_2$, which are useful in the preparation of polyimide and polyurethane polymers. In particularly, the invention relates to the use of benzoic acid, and substituted benzoic acids, to catalyze the condensation of two molecules of an aryl halide to yield the diaryl ether.

Our first attempts to form substituted diphenyl ethers from 4-nitro-2-(trifluoromethyl)chlorobenzene illustrated that the presence of the trifluoromethyl group led to unexpected side reactions. These experiments were conducted using potassium carbonate as the base and 4-chlorobenzoic acid as the catalyst. Various reactions were conducted in polar solvents such as dimethylacetamide (DMAc), at temperatures of 140° C.–150° C. or non-polar solvents, or even neat in the presence of phase transfer catalysts (18-crown-6, tetraphenylphosphonium bromide, or the methyl ethers of polyethylene glycols) at temperatures over 200° C. Unfortunately, an appreciable quantity of products such as 4-nitro-2-(trifluoromethyl)fluorobenzene were formed. Since there is no other source of fluorine, the appearance of these products indicated that there was some decomposition of the trifluoromethyl group. In addition, compounds such as bis ether were formed (see comparative example 3). As further elaborated below, the bis ether is a useful chemical intermediate.

The halogen in the starting material may be F, Cl, Br or I. The starting material may be prepared by the nitration of a 2-(trifluoromethyl)halobenzene. The chloro compound, that is 4-nitro-2-(trifluoromethyl)chlorobenzene, is commercially available. As generally prepared, and as available commercially, the predominant isomer is 4-nitro isomer. However, there is significant amounts of 2-nitro-6-(trifluoromethyl)chlorobenzene. The structure of these two isomers are:

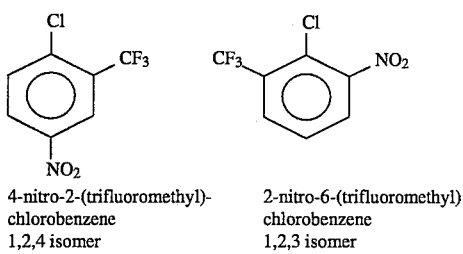

4-nitro-2-(trifluoromethyl)-
chlorobenzene
1,2,4 isomer 2-nitro-6-(trifluoromethyl)
chlorobenzene
1,2,3 isomer The ether formed from 1,2,3 isomer is not as desirable, for many purposes, as that formed from the predominant isomer. As will be seen below, it is best to run the process in such a manner as to limit the amount of 1,2,3 isomer which enters into the reaction.

The reaction is run between about 140° C. and 220° C. A small amount of water is required in order for the reaction to occur. However, water generally need not be added to the reaction since either the base, or the ingredients themselves, generally contain sufficient water for the reaction to occur. Accordingly, the addition of extra water is hardly ever necessary. The overall equation for the reaction is:

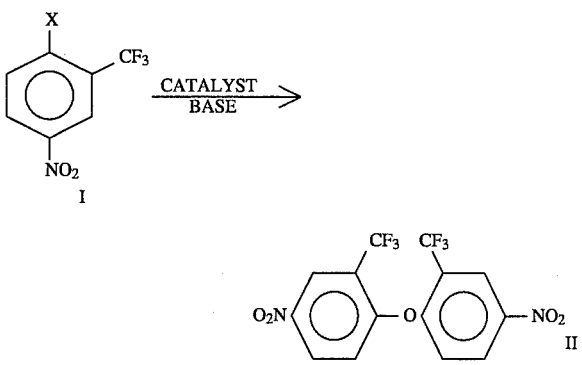

where X is F, Cl, Br, or I.

The reaction may be conducted in a non polar solvent with a boiling point of greater than about 200° C. Alternatively the reaction may be run in a non-polar solvent of lower boiling point provided that it is run under sufficient pressure to achieve the temperatures necessary for the reaction. Among the non-polar solvents which may be used are aromatic hydrocarbons such as benzene, toluene, xylene, and chlorinated aromatic hydrocarbons such as trichlorobenzene, dichlorobenzene and α-chloronaphthalene.

When the reaction is run in a non-polar solvent, a phase transfer catalyst, such as the methyl ether of polyethylene glycols, crown ethers, phosphonium salts, or ammonium salts is required. Generally speaking, a phase transfer catalyst is a chemical species which combines, within the same molecule both a polar and a non-polar end. Such molecules allow polar species to exist in non-polar solvents. The reaction may be conducted in the absence of a solvent using a phase transfer catalyst and conditions similar to those used for a non-polar solvent.

The reaction may be run in a dipolar aprotic solvent. In this case, no phase transfer catalyst are required. Among the solvents which are useful are dimethyl acetamide, dimethyl formamide, N-methyl pyrrolidone, dimethyl sulfoxide, and sulfolane. As noted above, a very small amount of water is required for the reaction to proceed. However, most dipolar aprotic solvents contain more water than is required for the reaction. The presence of excess water can lead to side reactions which result in the formation of undesired products. Accordingly, when the reaction is conducted in a dipolar or aprotic solvent, care should be taken to assure that the solvent is reasonably dry. However, good yields may be obtained at water concentrations below 10%.

Alkali metal hydroxides, carbonates, and bicarbonates are suitable bases for conducting this reaction. The carbonates are the preferred bases. Although potassium carbonate and sodium carbonate are usable, cost considerations and ease of processing make sodium carbonate the preferred base. As indicated above, the product formed from the 1,2,3 isomer is not generally desirable. The sodium bases tend to be more discriminating and result in less incorporation of the 1,2,3 isomer. In addition, the trifluoromethyl group seems more likely to decompose when potassium salts are used. Whatever base is selected, it is important that there be approximately one equivalent of base used. Larger quantities of base lead to side reactions and, accordingly, are undesirable.

Benzoate catalysts, that is, substituted benzoic acids containing one or more electron withdrawing substituents, and salts of substituted benzoic acids with one or more electron withdrawing substituents all catalyze the reaction of the aryl halides to form ethers. Electron withdrawing substituents include F, Cl, Br, I, $NO_2$, CN, $CF_3$, and other such groups well known to those skilled in the art. Any benzoate catalyst which is stable under the reaction conditions may be used as a catalyst for this reaction. For example, all isomers of benzoic acids such as the chlorobenzoic acids, bromobenzoic acids, fluorobenzoic acids, dichlorobenzoic acids, dibromobenzoic acids, tribromobenzoic acids, trichlorobenzoic acids, trifluoromethylbenzoic acids, nitrobenzoic acids, dinitrobenzoic acids, or salts of any of the above acids may be used as catalysts for this reaction. The catalyst is effective in amounts of about 0.1 mole % or more. The catalytic effect of the benzoate is illustrated by comparing a reaction run without benzoate, with a similar reaction run in the presence of a benzoate. This can be readily seen by examining the results shown in Comparative Example 1, compared to the results shown by Example 4. The comparative example, run without benzoate catalyst, shows much poorer yields and slower conversion than is shown by the same reaction run with the benzoate catalyst.

The formation of bis ether may be controlled by two means. One method is to use sodium hydroxide, sodium carbonate or sodium bicarbonate as the base in conjunction with a benzoate catalyst with one or more strongly electron withdrawing groups such as nitro. Thus, the use of nitro benzoic acid as a catalyst tends to lessen the formation of bis ether compared to chlorobenzoic acid. In addition, if the reaction is run to lower conversions of starting material to products (for example 60–70% conversion), bis ether formation is not observed. Potassium hydroxide, carbonate, or bicarbonate is a suitable base even in combination with an acid catalyst such as chlorobenzoic acid provided that the reaction is run to a lower degree of conversion. The degree of conversion can readily be determined during the course of the reaction through the use of gas chromatography.

The product of this reaction may be isolated by filtering the reaction mixture to remove inorganic matter and evaporating the solvent. The resulting product may be crystallized from an alcohol such as methanol or ethanol. Other methods of isolation and purification will be apparent to those skilled in the art.

The bis ether may be reduced to form bis ether diamine which is useful as an intermediate in the preparation of polyimides and polyurethanes. Reduction may be accomplished by formate in the presence of a palladium on charcoal catalyst, hydrogen gas in the presence of a palladium on charcoal catalyst, iron metal and hydrochloric acid, or several other methods well known to those skilled in the art.

The bis ether diamine may be reacted with a wide variety dianhydrides to form polyimide resins. These polyimides have desirable electrical properties and are useful for applications such as insulation of wires and other objects, and coating circuit boards. The formation of the polymer is a two step process. In the first step, the dianhydride reacts with the bis ether diamine to form a polyamic acid which generally remains in solution. The polyamic acid solution is then subjected to a curing process which may include heat. If heat is used the solvent evaporates, and the polyamic acid releases water to form the final polyimide. Chemical methods of curing are also available. Among the dianhydrides suitable for the preparation of polyimides from bis ether diamine are: bisphenol S dianhydride, bisphenol A dianhydride, thiodiphthalic anhydride, 4,4'-oxydiphthalic anhydride, sulphonyldiphthalic anhydride, sulphoxydiphthalic anhydride, symmetrical biphenyl dianhydride, un-symmetrical biphenyl dianhydride, pyromellitic dianhydride, benzophenone tetracarboxylic dianhydride, resorcinol dianhydride, hydroquinone dianhydride. The polyimides formed have the following recurring structure:

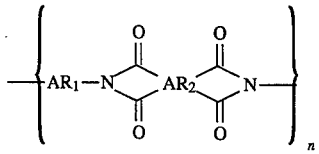

Where $AR_2$ is

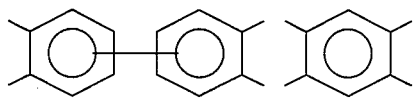

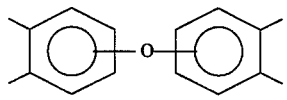

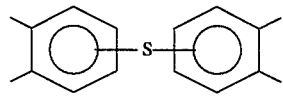

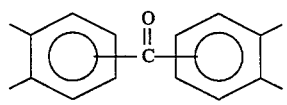

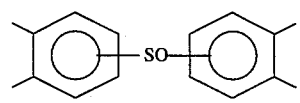

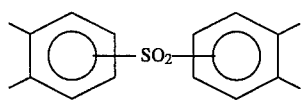

-continued

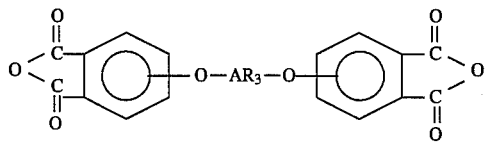

WHERE $AR_3$ IS

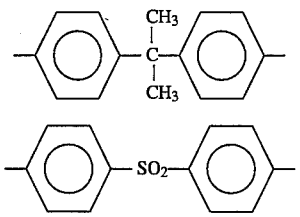

and $AR_1$ is

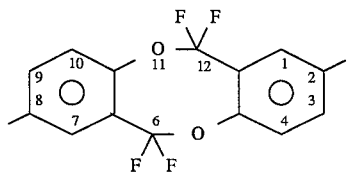

EXAMPLES

Example 1

4-nitro-2-(trifluoromethyl)chlorobenzene (20.00 g, 88.7 mmol), 3-nitrobenzoic acid (0.0694 g, 0.005 eq.) and sodium carbonate (4.61 g, 1.0 eq.) in dimethyl acetamide (30 mL) were stirred mechanically under a nitrogen atmosphere at 150° C. After 27 hours, gas chromatographic (GC) analysis showed that the conversion was 96.0% and the gas chromatographic analysis with internal standard (GC ISTD) yield of 4,4'-dinitro-2,2'-bis(trifluoromethyl)diphenyl ether was 86.4%. The reaction mixture was filtered to remove inorganic salts and the resulting filtrate was concentrated to give a red solid. Recrystallization from methanol gave 4,4'-dinitro-2,2'-bis(trifluoromethyl)diphenyl ether as a beige solid (13.61 g, 81.2% yield, GC purity 99.9+%).

Example 2

4-nitro-2-(trifluoromethyl)chlorobenzene (20.00 g, 88.7 mmol), the sodium salt of 4-nitrobenzoicacid (0.08 g, 0.005 eq.) and sodium carbonate (6.12 g, 1.0 eq.) in dimethyl acetamide (30 mL) were stirred mechanically under a nitrogen atmosphere at 150° C. After 45 hours, the conversion was 96.7% and the GC yield of 4,4'-dinitro-2,2'-bis(trifluoromethyl)diphenyl ether was 91.9%.

Example 3

4-Nitro-2-(trifluoromethyl)chlorobenzene (20.00 g, 88.7 mmol), 3,4-dinitrobenzoic acid (0.0940 g, 0,005 eq.) and sodium carbonate (4.61 g, 1.0 eq.) in dimethyl acetamide (30 mL) were stirred mechanically under a nitrogen atmosphere at 150° C. After 27 hours GC analysis showed that the conversion was 96.0% and the GC ISTD yield of 4,4'-dinitro-2,2'-bis(trifluoromethyl) diphenyl ether was 86.4%.

Example 4

4-Nitro-2-(trifluoromethyl)chlorobenzene (1.13 g, 5.0 mmol), potassium carbonate (0.350 g, 1.0 eq.) and 4-chlorobenzoic acid (0.014 mg, 0.01 eq.) were heated under nitrogen at 160° C. in DMAc. After 2 hours the yield by GC of 4,4'-dinitro-2,2'-bis(trifluoromethyl)diphenyl ether was 65.4% and the conversion was 65.4%.

Example 5

4-Nitro-2-(trifluoromethyl)chlorobenzene (2.25 g, 10.0 mmol), potassium carbonate (0.710 g, 1.03 eq.), 4-chlorobenzoic acid (0.14 g, 0.01 eq.) and 18-crown-6 (0.13 g, 0.5% by weight) were heated at 210° C. After 2 hours the GC yield of 4,4'-dinitro-2,2'-bis(trifluoromethyl)diphenyl ether was 62% and the conversion was 62%.

Example 6

4-nitro-2-(trifluoromethyl)chlorobenzene (2.25 g, 10.0 mmol), potassium carbonate (0.710 g, 1.03 eq.), 4-chlorobenzoic acid (0.28 g, 0.02 eq.) and hexyl-triphenylphosphonium bromide (0.058 g, 2.5% by weight), were heated at 210° C. After 2 hours the GC yield of 4,4'-dinitro-2,2'-bis(trifluoromethyl)diphenyl ether was 24.8% and the conversion was 25.9%.

Comparative Example 1

4-Nitro-2-(trifluoromethyl)chlorobenzene (1.13 g, 5.0 mmol), and potassium carbonate (0.350 g, 1.0 eq.) were heated under nitrogen at 160° C. in DMAc. These were the same conditions used in example 4, except no 4-chlorobenzoic acid had been added to catalyze ether formation. After 2 hours the yield by GC of 4,4'-dinitro-2,2'-bis(trifluoromethyl)diphenyl ether was 4.2% and the conversion was 4.2%.

Comparative Example 2

4-Nitro-2-(trifluoromethyl)chlorobenzene (2.25 g, 10.0 mmol), potassium carbonate (0.710 g, 1.03 eq.) and 4-chlorobenzoic acid (28 mg, 0.02 eq.) were heated at 180° C. for 24 hours; GC analysis revealed no reaction had occurred. After raising the temperature to 210° C. for 7 hours, the GC yield of 4,4'-dinitro-2,2'-bis(trifluoromethyl)diphenyl ether was 4.1% and the conversion was 5.3%.

Comparative Example 3

4-Nitro-2-(trifluoromethyl)chlorobenzene (100.00 g, 0.443 mole), potassium carbonate (64.33 g, 2.1 eq.) and 4-chlorobenzoic acid (1.00 g, 0.015 eq.) were heated under nitrogen to 140° C.–150° C. in dimethyl formamide in a 3 neck round bottom flask equipped with a mechanical stirrer. After 17 hours, GC analysis showed high conversion (97.6%) of 4-nitro-2-(trifluoromethyl)chlorobenzene; however, the ratio of 4,4'-dinitro-2,2'-bis(trifluoromethyl)diphenyl ether: bis ether formed was 78:22.

Comparative Example 4

4-Nitro-2-(trifluoromethyl)chlorobenzene (20.00 g, 88.7 mmol), 4-nitrobenzoic acid (0.278 g, 0.02 eq.) potassium carbonate (6.12 g, 1.0 eq.), methylated polyethylene glycol, MW=2000 (MPEG-2000) (0.60 g, 3% by weight) and 1,2,4-trichlorobenzene (6.7 g, 25% by weight) were heated at 209° C. under nitrogen for 4 hours. GC analysis at 2 hours showed 79.6% conversion with major product being the desired 4,4'-dinitro-2,2'-bis(trifluoromethyl)diphenyl ether (69% by GC) GC analysis at 4 hours revealed a conversion of 86 8% but the major product was 4-nitro-2-(trifluoromethyl)fluorobenzene (71% by GC).

We claim:

1. A process for the preparation of 4,4'-dinitro-2,2'-bis-(trifluoromethyl)diphenyl ether comprising reacting a compound of the formula

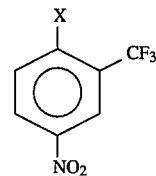

where X is F, Cl, Br, or I with approximately one equivalent of an inorganic base selected from the group consisting of alkali metal hydroxides, alkali metal carbonates, and alkali metal bicarbonates, in the presence of at least about 0.1 mole % of a benzoate catalyst selected from the group consisting of 4-chlorobenzoic acid, 3-nitrobenzoic acid, 4-nitrobenzoic acid, 3,5-dinitrobenzoic acid, and 3,5-dichlorobenzoic acid, and a small amount of water.

2. A process for the preparation of 4,4'-dinitro-2,2'-bis-(trifluoromethyl)diphenyl ether comprising reacting in a non-polar solvent in the presence of a phase transfer catalyst a compound of the formula

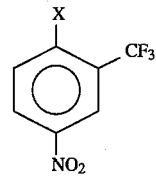

where X is F, Cl, Br, or I with approximately one equivalent of an inorganic base selected from the group consisting of alkali metal hydroxides, alkali metal carbonates, and alkali metal bicarbonates, in the presence of at least about 0.1 mole % of a benzoate catalyst and a small amount of water.

3. A process according to claim 2 wherein the inorganic base is selected from the group consisting of sodium carbonate and potassium carbonate.

4. A process according to claim 3 wherein the benzoate catalyst is 4-chlorobenzoic acid.

5. A process according to claim 3 wherein the benzoate catalyst is 3-nitrobenzoic acid.

6. A process according to claim 3 wherein the benzoate catalyst is 4-nitrobenzoic acid.

7. A process according to claim 3 wherein the benzoate catalyst is 3,5-dinitrobenzoic acid.

8. A process according to claim 3 wherein the benzoate catalyst is 3,5-dichlorobenzoic acid.

9. A process according to claim 2 wherein the reaction temperature is between about 140° C. and 220° C.

10. A process according to claim 2 including the additional last steps of isolating said 4,4'-dinitro-2,2'-bis(trifluoromethyl)diphenyl ether and reducing it to 4,4'-diamino-2, 2'-bis(trifluoromethyl)diphenyl ether.

11. A process according to claim 2 wherein the amount of said benzoate catalyst is up to about 2 mole %.

12. A process for the preparation of 4,4'-dinitro-2,2'-bis(trifluoromethyl)diphenyl ether comprising reacting in a polar aprotic solvent a compound of the formula

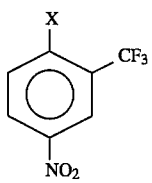

where X is F, Cl, Br, or I, with approximately one equivalent of an inorganic base selected from the group consisting of sodium carbonate and potassium carbonate in the presence of at least about 0.1 mole % of a benzoate catalyst selected from the group consisting of 4-chlorobenzoic acid, 3-nitrobenzoic acid, 4-nitrobenzoic acid, 3,5-dinitrobenzoic acid, and 3,5-dichlorobenzoic acid, and a small amount of water.

13. A process according to claim 12 wherein the reaction temperature is between about 140° C. and 220° C.

14. A process according to claim 12 including the additional last steps of isolating said 4,4'-dinitro-2,2'-bis(trifluoromethyl)diphenyl ether and reducing it to 4,4'-diamino-2,2'-bis(trifluoromethyl)diphenyl ether.

15. A process according to claim 12 wherein the amount of said benzoate catalyst is up to about 2 mole %.

16. A process for the preparation of 4,4'-dinitro-2,2'-bis(trifluoromethyl)diphenyl ether comprising reacting in the absence of a solvent a compound of the formula

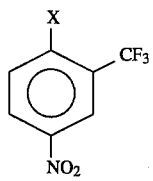

where X is F, Cl, Br, or I with approximately one equivalent of an inorganic base selected from the group consisting of alkali metal hydroxides, alkali metal carbonates, and alkali metal bicarbonates, in the presence of at least about 0.1 mole % of a benzoate catalyst and a small amount of water.

17. A process according to claim 16 wherein the inorganic base is selected from the group consisting of sodium carbonate and potassium carbonate.

18. A process according to claim 16 wherein the benzoate catalyst is 4-chlorobenzoic acid.

19. A process according to claim 16 wherein the benzoate catalyst is 3-nitrobenzoic acid.

20. A process according to claim 16 wherein the benzoate catalyst is 4-nitrobenzoic acid.

21. A process according to claim 16 wherein the benzoate catalyst is 3,5-dinitrobenzoic acid.

22. A process according to claim 16 wherein the benzoate catalyst is 3,5-dichlorobenzoic acid.

23. A method of making 4,4'-dinitro-2,2'-bis(trifluoromethyl)diphenyl ether comprising (A) preparing a mixture of (1) a compound having the formula

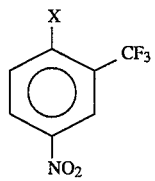

where X is F or Cl;
(2) approximately one equivalent of sodium carbonate;
(3) a small amount of water; and
(4) at least about 0.1 mole % of a benzoate catalyst selected from the group consisting of 4-chlorobenzoic acid, 3-nitrobenzoic acid, 4-nitrobenzoic acid, 3,5-dinitrobenzoic acid, and 3,5-dichlorobenzoic acid; and (B) heating said mixture to about 140° to about 220° C.

24. A method of preferentially reacting 4-nitro-2-(trifluoromethyl)-chlorobenzene in a mixture with 2-nitro-6-(trifluoromethyl)-chlorobenzene to form 4,4'-dinitro-2,2'-bis(trifluoromethyl)diphenyl ether comprising (a) adding to said mixture (1)

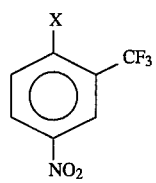

where X is F or Cl;
approximately one equivalent of a base selected from the group consisting of sodium hydroxide, sodium carbonate, and sodium bicarbonate; and (2) at least about 0.1 mole % of a benzoate catalyst selected from the group consisting of 4-chlorobenzoic acid, 3-nitrobenzoic acid, 4-nitrobenzoic acid, 3,5-dinitrobenzoic acid, and 3,5-dichlorobenzoic acid; and (b) heating said mixture to about 140° to about 220° C.

25. A method according to claim 24 wherein said base is sodium carbonate.

26. A method according to claim 25 including the additional last steps of isolating said 4,4'-dinitro-2,2'-bis(trifluoromethyl)diphenyl ether and reducing it to 4,4'-diamino-2,2'-bis(trifluoromethyl)diphenyl ether.

27. A method according to claim 24 wherein no solvent is present.

28. A method according to claim 24 wherein a non-polar solvent is present.

* * * * *